US005976075A

United States Patent [19]
Beane et al.

[11] Patent Number: 5,976,075
[45] Date of Patent: Nov. 2, 1999

[54] ENDOSCOPE DEPLOYMENT APPARATUS

[75] Inventors: Richard Beane, Hingham; Steven W. Ek, Bolton, both of Mass.; Paul Lucey, Salem, N.H.

[73] Assignees: University of Massachusetts, Boston; Smith & Nephew, Inc., Andover, both of Mass.

[21] Appl. No.: 08/991,018

[22] Filed: Dec. 15, 1997

[51] Int. Cl.$^6$ ........................................... A61B 1/00
[52] U.S. Cl. ........................ 600/146; 600/106; 600/112
[58] Field of Search ................................. 600/102, 106, 600/114, 125, 131, 141, 146, 149, 136

[56] References Cited

U.S. PATENT DOCUMENTS

| | | | |
|---|---|---|---|
| 3,270,641 | 9/1966 | Gosselin | 600/146 |
| 3,776,222 | 12/1973 | Smiddy | 600/146 |
| 4,195,624 | 4/1980 | Douglas | 600/114 |
| 4,593,679 | 6/1986 | Collins | 600/146 |
| 4,688,554 | 8/1987 | Habib | 600/114 |
| 4,911,148 | 3/1990 | Sosnowski | 600/136 |
| 5,140,975 | 8/1992 | Krauter | 600/146 |
| 5,275,151 | 1/1994 | Shockey | 600/146 |
| 5,325,845 | 7/1994 | Adair | 600/114 |
| 5,531,687 | 7/1996 | Snoke | 600/146 |
| 5,569,292 | 10/1996 | Scwemberger | 606/185 |
| 5,634,466 | 6/1997 | Gruner | 600/136 |
| 5,711,756 | 1/1998 | Chikama | 600/112 |
| 5,749,828 | 5/1998 | Solomon | 600/146 |
| 5,810,716 | 11/1996 | Mukherjee | 600/141 |

OTHER PUBLICATIONS

WO 96/27991, Oz, Dan, Sep. 12, 1996.

*Primary Examiner*—Linda C. M. Dvorak
*Assistant Examiner*—Ira Hatton

*Attorney, Agent, or Firm*—Lahive & Cockfield, LLP

[57] ABSTRACT

An endoscope system according to the present invention is characterized by an imaging assembly that a user can alternatively attach to a first deployment assembly and to a second deployment assembly. The image assembly has a distal end configured for detecting image information and a proximal end configured for delivering the image information to a location remote from the imaging assembly distal end. The deployment assembly for deploying the imaging assembly includes a support member and a connecting member. The connecting member is carried on the support member and is removably and replaceably mountable with the imaging assembly housing for connecting the support member to the imaging assembly. According to a preferred embodiment of the invention, the support member includes a shaft member, a handle element connected to the proximal end of the shaft member for manual engagement of the deployment assembly, an articulating portion connected to the distal end of the shaft member and movable between undeflected and deflected positions for deflecting the tip of the imaging assembly, and a deflecting element. The deflecting element is attached in selected proximity to the distal end of the articulating portion for deflecting the articulating portion. The deployment assembly can include an imaging assembly guide element slidably and removably and replaceably mountable with the imaging assembly. Thus, an operator can use her hand to slidably extend the imaging assembly from the deployment means so as to position the imaging assembly's distal end in selected proximity to a target site.

15 Claims, 11 Drawing Sheets

ENDOSCOPE DEPLOYMENT APPARATUS

The present application is related to our application Ser. No. 08/990,933, filed Dec. 15, 1997, entitled "Modular Camera System," currently pending (attorney docket number UMM-023).

BACKGROUND OF THE INVENTION

The present invention relates to surgical endoscopes and more particularly to endoscopes for use in minimally invasive surgery. Minimally invasive surgery is performed through a primary incision that is smaller than most traditional surgical openings. Such surgery relies on an endoscope for visualization of the operative field. A surgeon can insert the endoscope into a patient's body via the primary incision or via an alternative insertion point.

An endoscope includes any instrument inserted into the body to obtain a view of the interior of the body. However, an endoscope for minimally invasive surgery often includes a long, thin imaging assembly with an image detecting element located at the distal end of the assembly and electrically conductive leads extending from the image detecting element. Such endoscopes generally also include an illumination fiber bundle which brings light down to the region of the imaging or camera lens and which illuminates the field of view. An endoscope system for minimally invasive surgery will often display a video image on a large monitor.

Generally for thoracoscopic surgery, the viewing endoscope is handled and operated by a dedicated operating room assistant. The endoscope can have a short focal length and working distance allowing the operator to position the endoscope close to a surgical field when the surgeon makes incisions for harvesting a small vessel or when the surgeon removes a tissue specimen.

Thoracic endoscopes generally have a series of small diameter lenses, e.g., rod lenses, adapted to relay an image from an objective assembly to an eyepiece. Alternatively, thoracic endoscopes can have an objective which directly images onto a CCD element or video pick-up under about one centimeter in cross dimension. The optics may have a field of view between about 50° to over 100°, and a working distance generally on the order of one half to two inches. These specifications allow the camera to be sufficiently close to the surgical instrument to effectively image the details of the surgical field.

One drawback of a typical endoscope with a field of view of about 50° is that to obtain a sufficiently enlarged view of the surgical field so as to facilitate surgical tasks such as dissecting and suturing tissue, clipping vessels, and the like, the endoscope must be moved closer to the tissue and constantly re-positioned as the surgery proceeds. Advancing the endoscope narrows the actual view. In addition, when operating at a working distance of about one inch, the surgeon may have a distorted or partially obscured view of even a simple structure, such as a vessel or small nodule, or may lose track of where in the operating theater he is actually performing. It is then necessary to retract the endoscope to obtain a wider field of view.

In thoracoscopic surgery, it is important for the surgeon to have access to a wide field of view of the surgical field because a typical procedure can involve cutting into the chest wall to harvest one or more blood vessels, for example when performing cardiac bypass grafting. The chest cavity includes organs such as a patient's heart and lungs and numerous vascular structures. These organs and vascular structures can obstruct endoscopes with a narrow field of view. In some cases a surgeon inserts her fingertips through the primary incision. The surgeons fingertips can also obstruct the endoscopes view of the surgical field.

In addition, a wide field of view can be necessary, for example, to guide a surgical instrument to a surgical site when the instrument is inserted at a point remote from the endoscope insertion point. A surgeon can accomplish such a wide field of view by positioning the endoscope at an appropriate angle far enough from the surgical site and far enough from the instrument insertion point to bring both the surgical site and the instrument insertion point into its field of view.

A supplemental view can also be obtained by inserting a second endoscope through a second endoscope insertion point to view the surgical arena from a different vantage point or angle, or with different overall magnification or field of view. The manipulation of the second endoscope would then require care 1) to determine and to maintain the endoscope's position, 2) to keep the surgical site in the field of view, and 3) to correlate the site shown in one endoscope with the site imaged by the other. This manipulation is difficult because of the number of instruments and incisions already involved in an operation and the limited visibility of the surgical field due to the intervening structures present when performing a surgical intervention, such as a resection or the excavation of a vessel.

A number of devices or systems for obtaining adequate views have been previously proposed to address related problems in the field of laparoscopic or bronchoscopic surgery or endoscopic biopsies. Thus, endoscope system designers have proposed various arrangements of multiple imaging sites and corresponding video synchronization, or screen-within-a-screen processing for situations where operators insert an endoscope along a body passage and use the endoscope for mapping or viewing features on the passage.

However, the situation of viewing polyps in the colon, or other features within a tubular passage differs substantially from the problem posed by imaging a surgical arena in a relatively large body cavity, such as the chest cavity. In thoracoscopic procedures, for example, instruments are inserted and tissue excavation or resection is carried out in and around a variety of tissues, mobile or moving organs, or the surgeon's fingers. In the latter context, there is no natural channel guiding the endoscope. The extent of the operating arena may be quite large and include a number of occluding structures around the surgical site itself.

Furthermore, in many procedures, it is common to use several distinct endoscopes. For example, in thoracoscopy, a surgeon will often initiate a procedure using a flexible endoscope. The flexible endoscope blocks the left or right bronchus allowing greater visualization of the surgical field. Such a flexible endoscope typically costs between about $8,000 and about $12,000. Following this initiation of the procedure, a rigid endoscope is used for thoracoscopic examination of the thoracic cavity. Such a rigid endoscope typically costs between about $3,000 and about $5,000. In addition, a surgeon can require an articulating endoscope or a different optical angle scope. An articulating scope typically costs between about $3,000 and about $5,000.

Another drawback of present endoscope systems is the amount of light lost in the illumination fiber bundle. Typical illumination fiber bundles deliver approximately 40% of the light delivered to the bundle by the light source. Inefficient transmission of light from the light source by the illumination fiber bundle can limit the imaging capability of an endoscope.

Thus there remains a need for improvement in endoscopic systems for surgical use.

Accordingly it is an object of the present invention to provide an endoscope system configured for effective viewing in and around a variety of tissues, mobile or moving organs, and the surgeon's fingers.

It is a further object of the invention to provide an endoscope system that does not require multiple, expensive endoscopes to successfully and efficiently complete a surgical procedure.

It is another object of the invention to minimize light loss in an illumination fiber bundle.

Other objects of the invention will in part be obvious and will in part appear hereinafter.

SUMMARY OF THE INVENTION

An endoscope system according to the present invention is characterized by an imaging assembly which a user can alternatively attach to a first deployment assembly and to a second deployment assembly.

One embodiment of the endoscope system includes an imaging assembly, and a deployment assembly. The image assembly has a distal end configured for detecting image information and a proximal end configured for delivering the image information to a location remote from the imaging assembly distal end.

The imaging assembly includes: i) an image detecting element located at the distal end of the imaging assembly for detecting image information; ii) an image delivering element located at the proximal end of the imaging assembly for delivering the image information to a location remote from the image detecting element; iii) an elongated, flexible signal cable assembly extending therebetween; and iv) a housing surrounding at least a selected portion of the distal end of the imaging assembly.

The deployment assembly for deploying the imaging assembly includes a support member and a connecting member. The connecting member is carried on the support member and is removably and replaceably mountable with the imaging assembly housing for connecting the support member to the imaging assembly. Thus, a single imaging assembly is removably and replaceably mountable with any of a plurality of deployment assemblies.

According to a preferred embodiment of the invention, the support member includes a shaft member, a handle element, an articulating portion, and a deflecting element. The shaft member has first and second ends. The handle element is connected to the first end of the shaft member for manual engagement of the deployment assembly. The articulating portion is coupled to the second end of the shaft member and is movable between undeflected and deflected positions for deflecting the tip of the imaging assembly. The articulating portion has a distal end. The deflecting element is attached in selected proximity to the distal end of the articulating portion for deflecting the articulating portion.

The deployment assembly can include an imaging assembly guide element slidably and removably and replaceably mountable with the imaging assembly. Thus, an operator can use her hand to slidably extend the imaging assembly from the deployment means so as to position the imaging assembly's distal end in selected proximity to a target site.

The cable assembly can include a posable portion located in selected proximity to the imaging assembly's distal end for manually posing the imaging assembly distal end in selected proximity to a target site.

The articulating portion can include a multi-part structure for deflecting the tip of the imaging assembly. The multi-part structure can include a plurality of hingedly connected vertebrae collectively forming a spine for deflection of the articulating portion.

The deflecting element can include a deflecting cable affixed in selected proximity to the distal end of the articulating portion so that a proximal displacement of the deflecting cable relative to the articulating portion flexes the articulating portion. The deflecting cable can be a rigid wire or a flexible, braided cable.

The endoscope system can include a clear tip attached to the distal end of the imaging assembly. The clear tip can include a blade element extending outwardly from the tip for facilitating penetration of the tip into tissue. The endoscope system can include a lens protector pivotally connected to the distal end of the imaging assembly for protecting the image detecting element during insertion of the distal end of the imaging assembly. Thus, an operator can remove the lens protector manually or otherwise from the central field of view of the image detecting means subsequent to insertion of the distal end of the imaging assembly.

The handle means can couple to the deflecting element for controlling the deflection of the articulating portion.

The handle mechanism can include a locking deflection control element coupled to the deflecting means for maintaining the deflection of the articulating portion.

The support member can include a soft-mount finger strap. Alternatively the support member can include a cannula.

DESCRIPTION OF THE ILLUSTRATED EMBODIMENTS

Figure 1A:
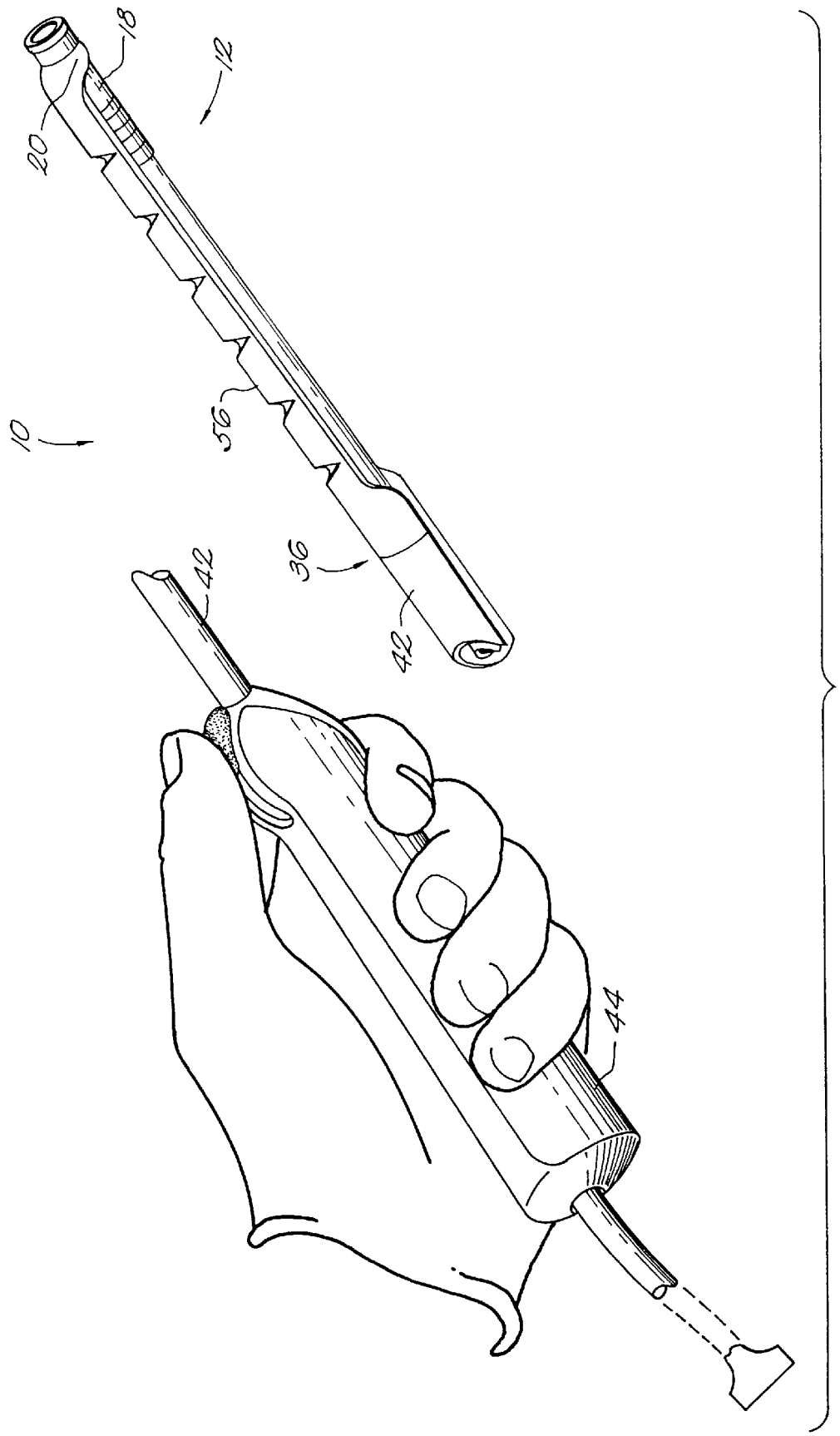
FIG. 1A is a perspective view of one embodiment of an endoscope system including an articulating deployment assembly according to the invention.
Figure 1B:
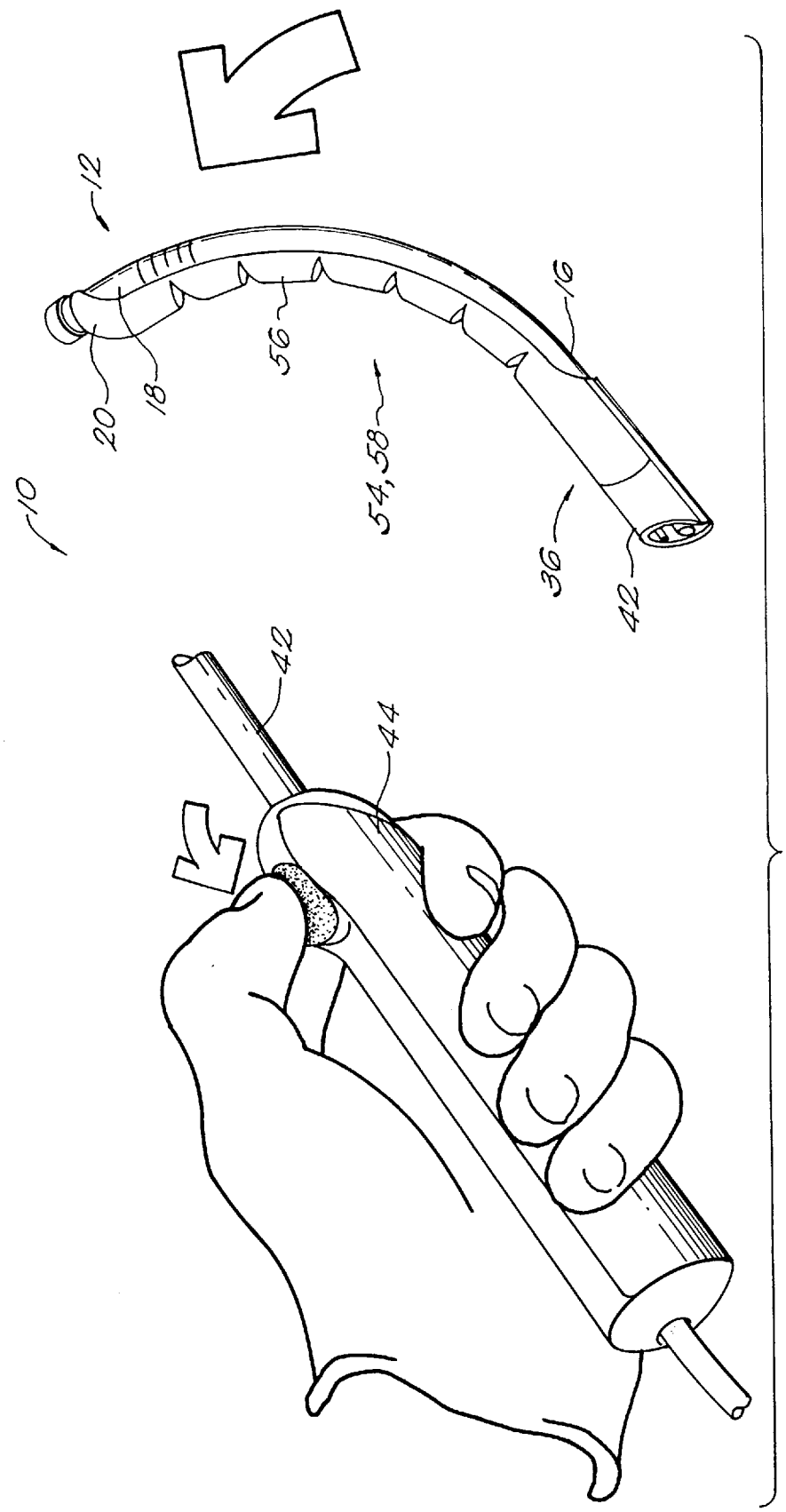
FIG. 1B is a perspective view of the endoscope system of FIG. 1A in a deflected position.
Figure 2:
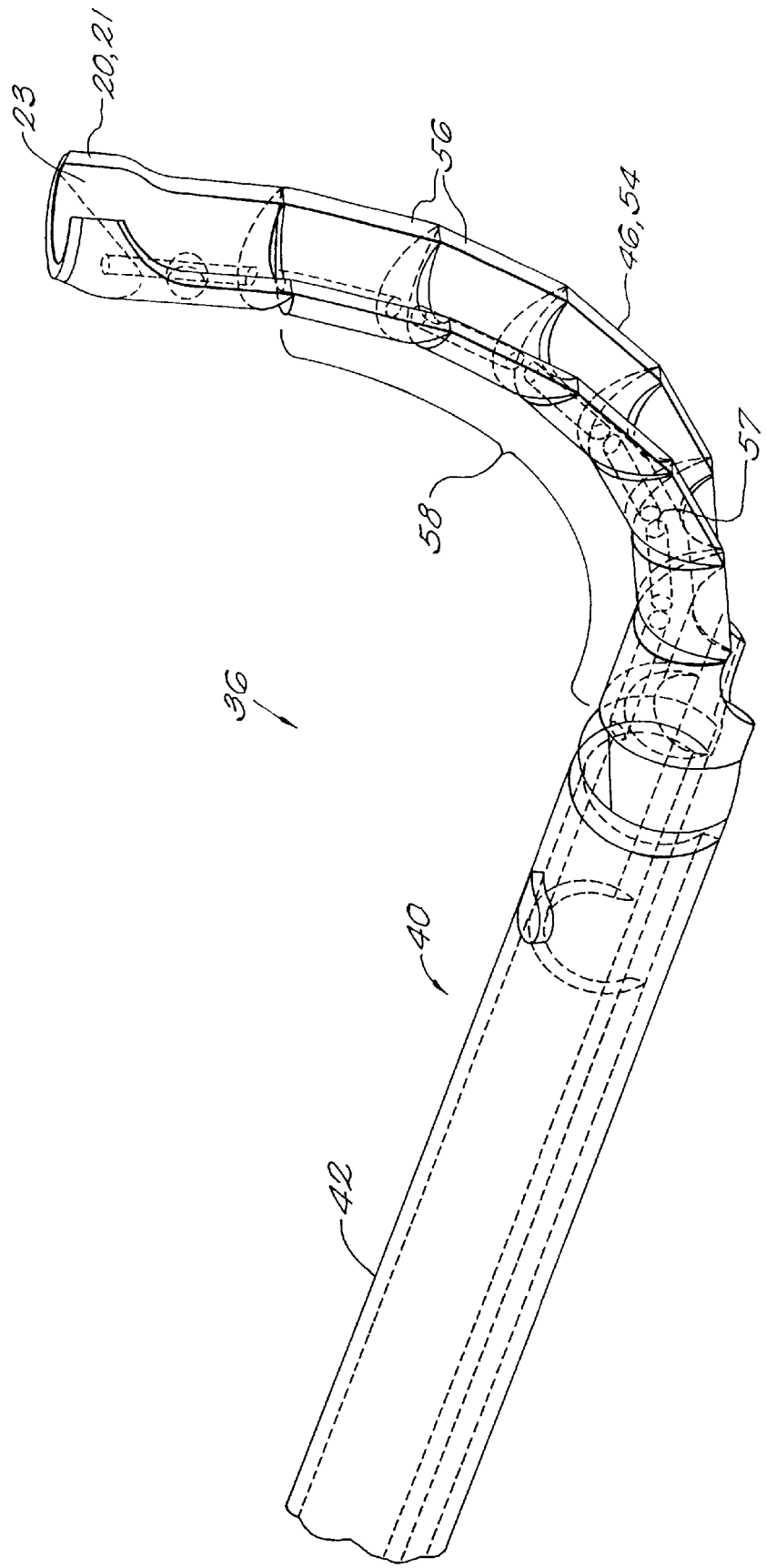
FIG. 2 is a skeleton view of the distal end of the articulating deployment apparatus of the endoscope of FIG. 1A.

FIGS. 1A and 1B show an arrangement of an endoscope system 10 having an imaging assembly 12 and a deployment assembly 36 according to one embodiment of the invention. FIG. 1A shows the endoscope system 10 in a first, undeflected position and FIG. 1B shows the endoscope system 10 in a second, deflected position.

With reference to FIGS. 1A, 3, 6 and 9, the imaging assembly 12 includes an image detecting element 14 located at the distal end of the imaging assembly, an image delivering element 19 located at the proximal end of the imaging assembly, an elongated, flexible signal cable assembly 16 extending between the image detecting element and the image delivering element, and a housing 18 surrounding a portion of the distal end of the imaging assembly.

Figure 3:
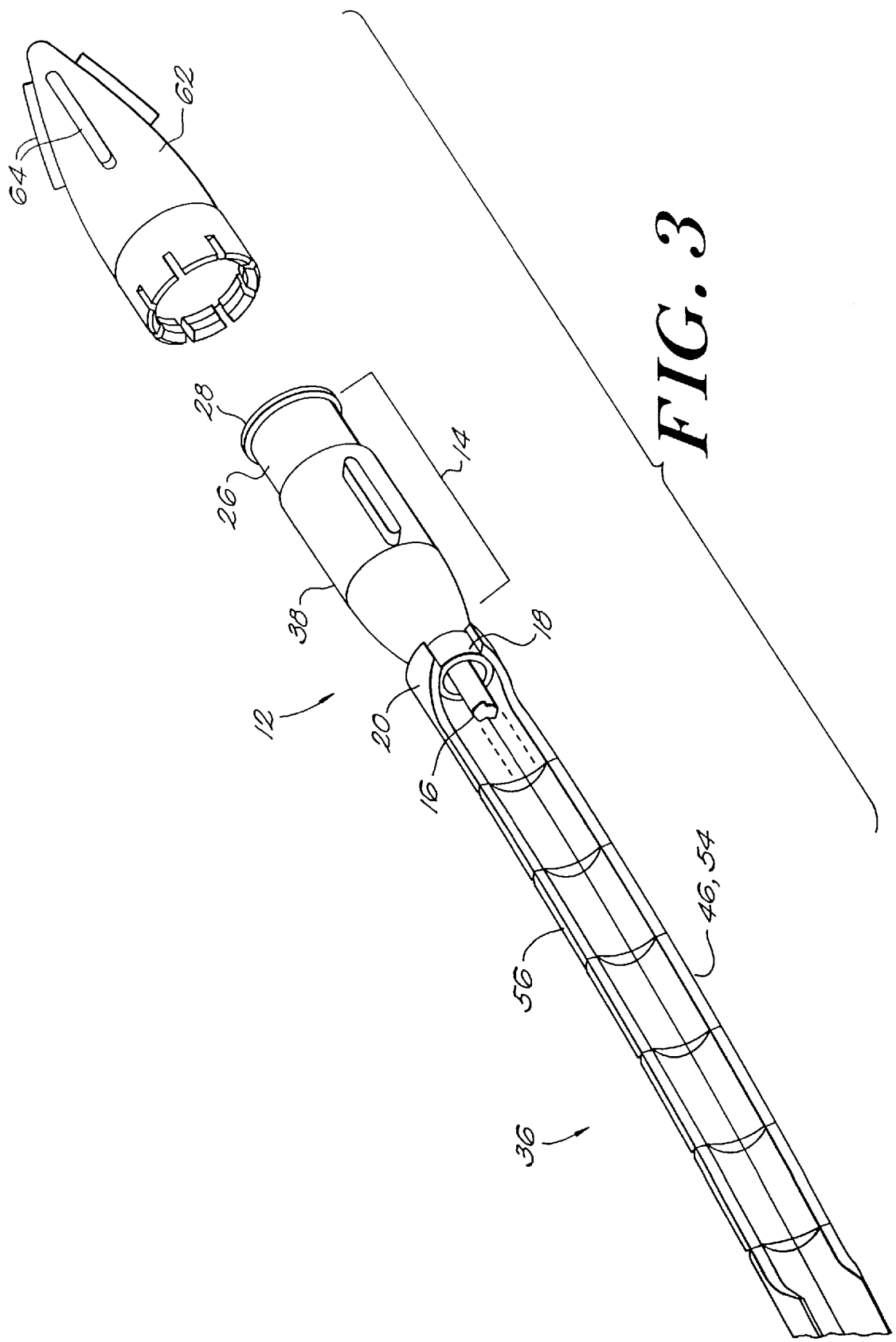
FIG. 3 is a perspective view of the endoscope system of FIG. 1A including a clear tip lens protector and a cut away view of an imaging assembly.
Figure 8A:
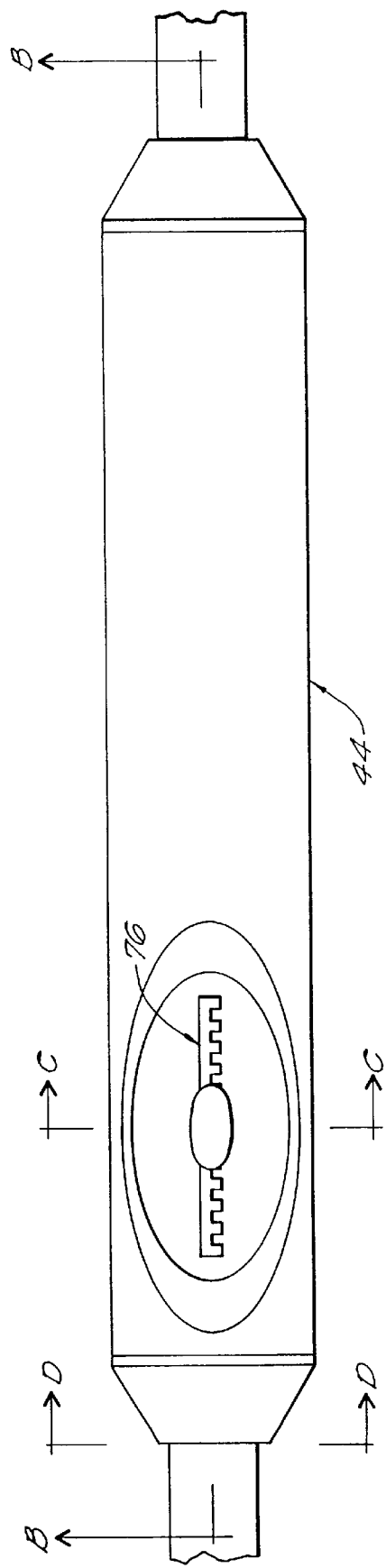
FIG. 8A is view from above of the handle mechanism of the endoscope system of FIG. 1A.
Figure 8B:
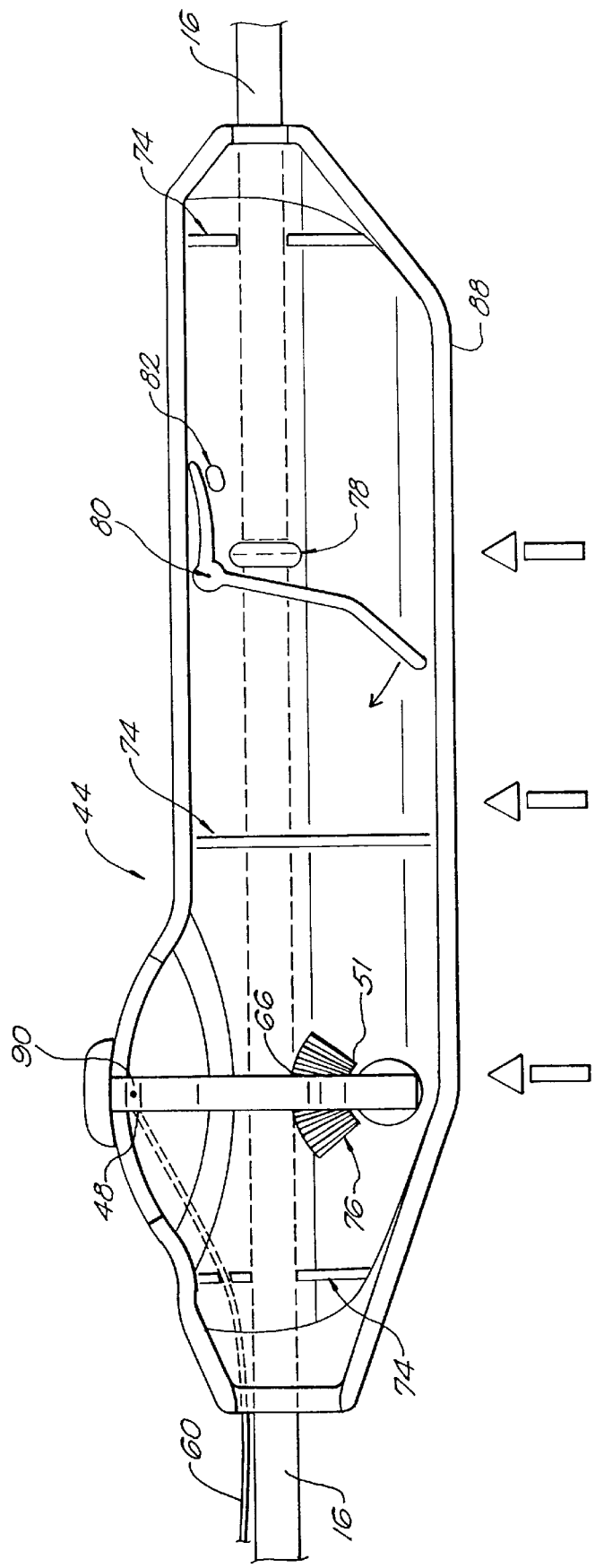
FIG. 8B is a side cross-sectional view, along section B—B of FIG. 8A, of the handle mechanism of the endoscope system of FIG. 1A.
Figure 8C:
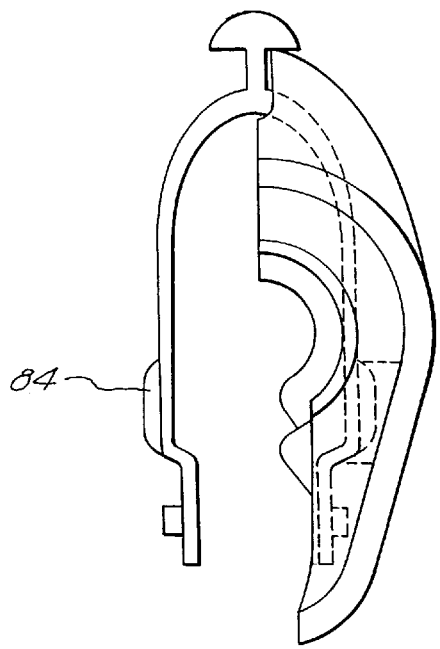
FIG. 8C is a longitudinal cross-sectional view, along section C—C of FIG. 8A, of the handle mechanism of the endoscope system of FIG. 1A.
Figure 8D:
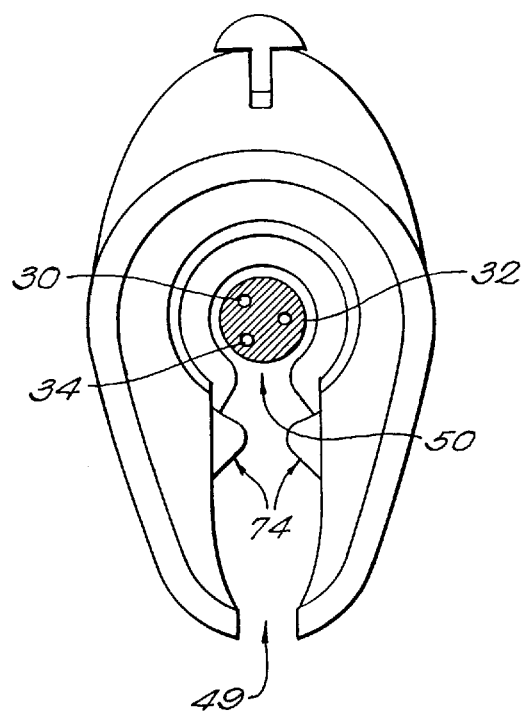
FIG. 8D is a longitudinal cross-sectional view, along section D—D of FIG. 8A, of the handle mechanism of FIG. 1A.
Figure 8E:
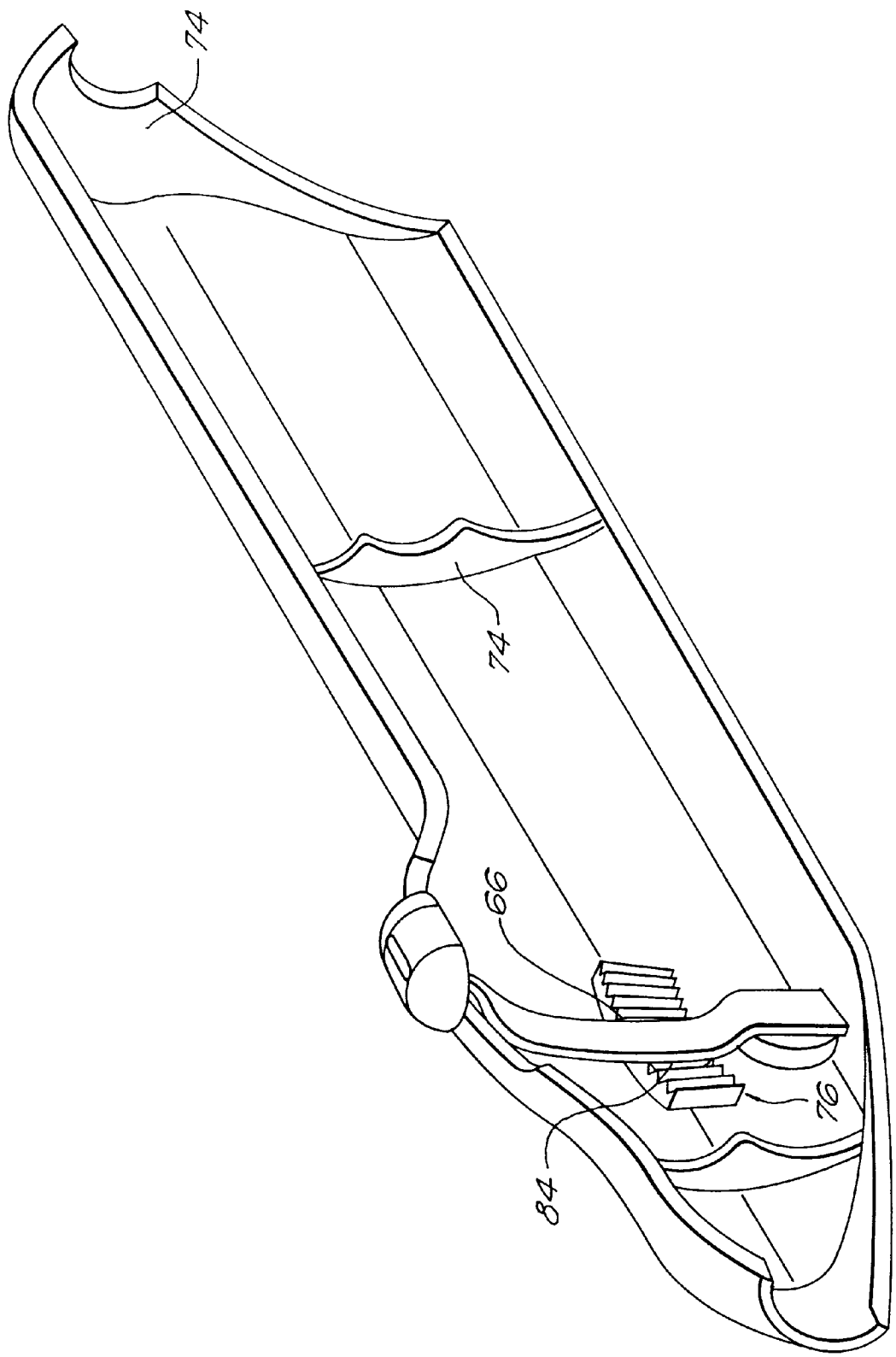
FIG. 8E is a perspective fragmentary view of the handle mechanism of FIG. 8A.

According to the illustrated embodiment, the image detecting element 14 includes a distal lens 28 and a charge coupled device (CCD) 26. With reference to FIG. 8D, the cable assembly 16 includes a fiber optic cable 30, an electronics cable 32 and an air or water conduit 34. In a preferred embodiment, the imaging assembly includes a molded body 38, as shown in FIG. 3 to seal the above-described components. With reference to FIG. 8B, the cable assembly can also include an overmolded feature 78 to facilitate operation of the deployment assembly 36 as described below.

With reference to FIGS. 1–3A and 8A–8E, the illustrated embodiment of the deployment assembly 36 includes a support member 40 and a connecting member 20. The support member 40 supports the imaging assembly 12 and the connecting member removably and replaceably mounts onto the imaging assembly, connecting the deployment assembly 36 to the imaging assembly 12.

According to one embodiment, the support member includes a shaft member 42, a handle assembly 44 attached to the proximal end of the shaft member 42, an articulating portion 46 coupled to the distal end of the shaft member 42, and a connecting member 20 carried on the support member. The support member further includes a deflecting assembly 48, as shown in FIG. 8B.

The handle assembly 44 of the embodiment illustrated in FIGS. 8A to 8E includes a handle housing 88, retaining ribs 74, a portion of the deflecting assembly 48, and a pivot/spring arm 80 biased by a boss 82. The deflecting assembly 48 has a deflecting cable 60 attached at one end to the distal end of the articulating portion and at the other end to a ratchet and pawl mechanism 51. The ratchet and pawl mechanism includes a lever 90 having a pawl 84, and a ratchet 76. The deflecting cable can be, among other cables, a rigid wire or a braided stainless steel cable that is approximately as flexible as a piece of string but much stronger.

Referring to the embodiment illustrated in FIGS. 1A to 3, the articulating portion includes a multi-part structure 54. The multi-part structure can include, among other elements, the illustrated segments or vertebrae 56. The segments 56 are hingedly connected along one side forming a spine 58. A hole 57 runs through each of the segments. The holes are aligned so that the deflecting cable can run through the segments substantially parallel to the cable assembly. Further, a portion of the material of the segments on the side opposite the spine are cut away allowing one segment to deflect relative to another.

Again with reference to the illustrated embodiment of FIGS. 8A to 8E, the cable assembly of the imaging assembly slips into the handle assembly through a cable insertion channel 49. The cable assembly has an overmolded feature 78, which is captured by the pivot/spring arm 80. The cable assembly snaps into the handle assembly as the cable assembly passes the retaining ribs 74. In other words, the retaining ribs 74 maintain the cable assembly 16 in the handle assembly 44. According to an alternative embodiment, the cable assembly 16 does not include an overmolded feature 78 and the retaining ribs 74 form an imaging assembly guide element 50 that slidably and removably and replaceably mounts with the cable assembly 16.

With reference to the embodiment illustrated in FIG. 3, the connecting member 20 is a C-shaped biased clip. However, the connecting member can take the form of any element capable of removably and replaceably mounting with the imaging assembly.

Thus, in the embodiment illustrated in FIGS. 1A–3 and 8A–8E, an imaging assembly 12 is mounted in a deployment assembly 36 by means of the connecting member 20 and the retaining ribs 74 of the handle assembly 44. In order to deflect the distal end of the endoscope system 10, an operator can adjust the position of the lever 90 of the deflecting assembly 48. The deflection of the lever 90 places tension on the deflecting cable 60 which is attached at the distal end of the articulating portion 46. The tension caused by the deflecting cable 60 deflects the articulating portion at each bend point.

The articulating endoscope system can return to an undeflected position in at least two ways. As in the illustrated embodiment of FIGS. 8A to 8E, the connecting member 20 and the pivot/spring arm 80 can maintain the cable assembly 16 under tension. That is the pivot/spring arm 80 applies axial tension on the cable assembly 16 via the overmolded feature 74 of the cable assembly. This tension tends to maintain the articulating portion 46 of the deployment assembly 36 in an undeflected position.

Alternatively, the deflecting cable can be a rigid wire. In this case, distal movement of the rigid wire relative to the articulating portion can return the system to an undeflected position.

Figure 9:
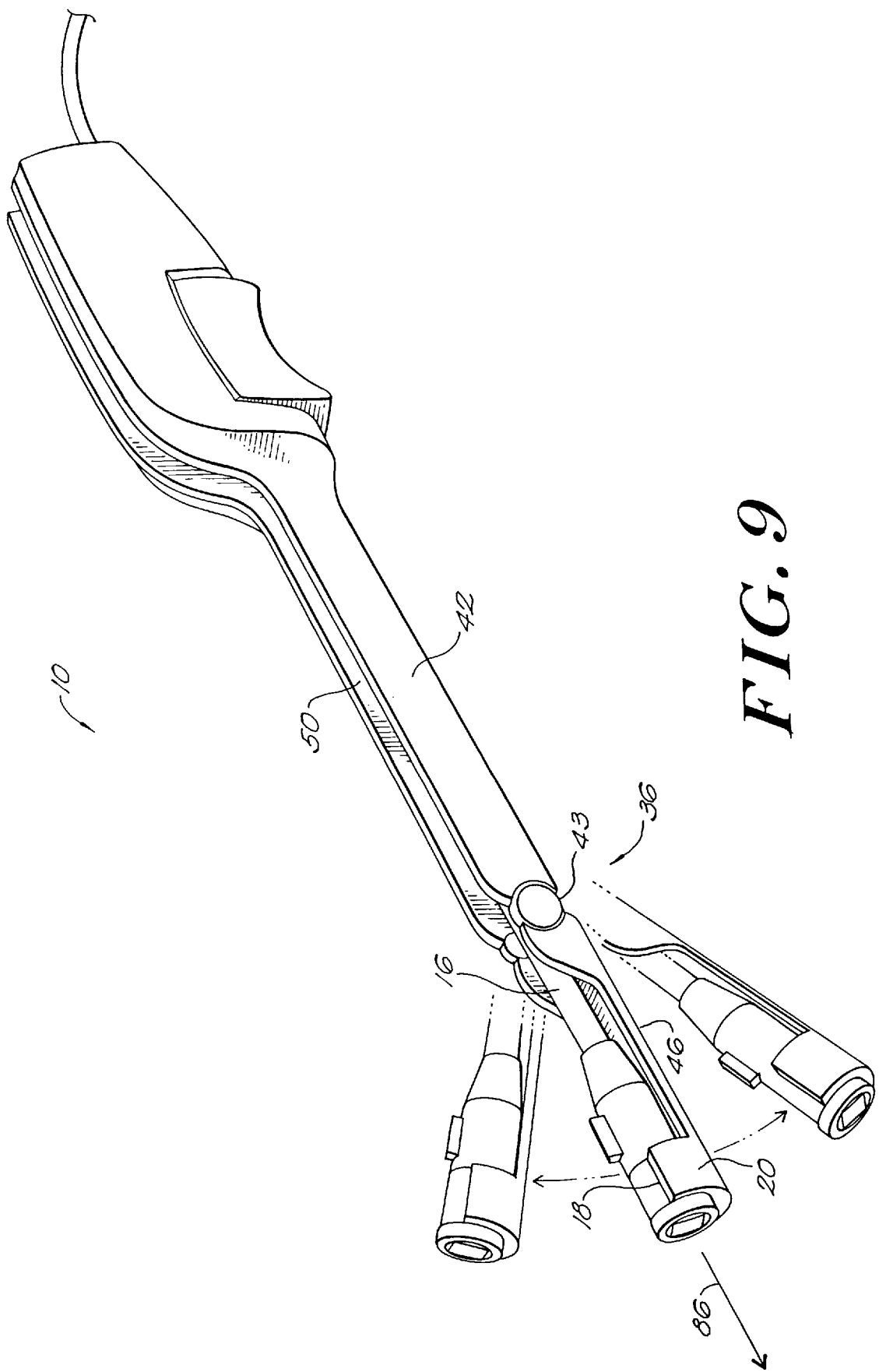
FIG. 9 is a perspective view of an alternative embodiment of the endoscope system of FIG. 1A.

Another embodiment of an articulating deployment assembly according to the invention is shown in FIG. 9. According to this embodiment, the articulating portion 46 is a single element, pivotally connected to the shaft member 42 by a pivot element 43. This version of an articulating deployment assembly carries a connecting member 20 removably and replaceably mountable with an imaging assembly.

According to yet another embodiment of the invention, an operator can manually and slidably extend the imaging assembly from the deployment assembly so as to position the imaging assembly's distal end in selected proximity to a target site. With reference to FIG. 9, the imaging assembly can slidably extend from the deployment assembly by sliding movement of the cable assembly 16 relative to the deployment assembly 36 along the deployment assembly's longitudinal axis 86. This embodiment is advantageous when a surgeon has her fingertips inserted into the patient's body. The surgeon can grasp the distal end of the imaging assembly, disconnect the distal end from the deployment assembly, and slidably extend the imaging assembly to view a target site.

Figure 7:
FIG. 7 shows an alternative version of the distal end of the imaging assembly of FIG. 1A including a posable portion.

Another embodiment of the imaging assembly as shown in FIG. 7 includes a posable portion 52 such that an operator can manually extend the imaging assembly from the deployment assembly and adjustably fix the position of the distal end of the imaging assembly. The posable portion includes a semi-rigid resilient tube 53, surrounding the distal end of the imaging assembly 12.

Referring to FIG. 3, one embodiment of the imaging assembly according to the invention can include a removable lens protector 62. The illustrated lens protector is clear and has a tapered, blunt nose to facilitate passage of the endoscope through various obstructions. The illustrated lens protector can include blade elements 64 to further facilitate passage of the endoscope through obstructions.

Figure 4:
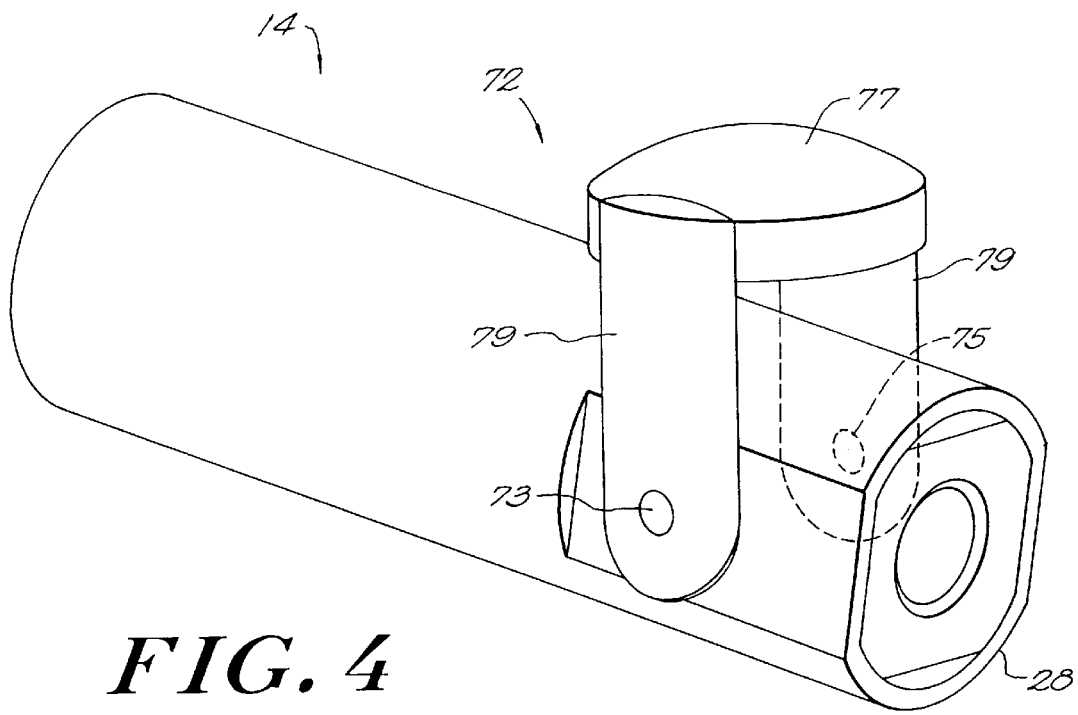
FIG. 4 is a perspective view of an alternative embodiment of the distal end portion of the imaging assembly of FIG. 1A.

An alternative lens protector assembly is illustrated in FIG. 4. A clear lens protector 77 has attachment posts 79 pivotally connected to the distal end of the imaging assembly 12 by pins 73 and 75. The center point of pin 75 is located further distally than the center point of pin 73. Thus, if an operator brings the lens protector 77 toward the tip of the device, a spring energy is created by the mismatch of the centers of the pins, causing the lens protector to either snap to the illustrated position or to a position in which the lens protector covers the lens 28 of the imaging detecting element 14.

Figure 5:
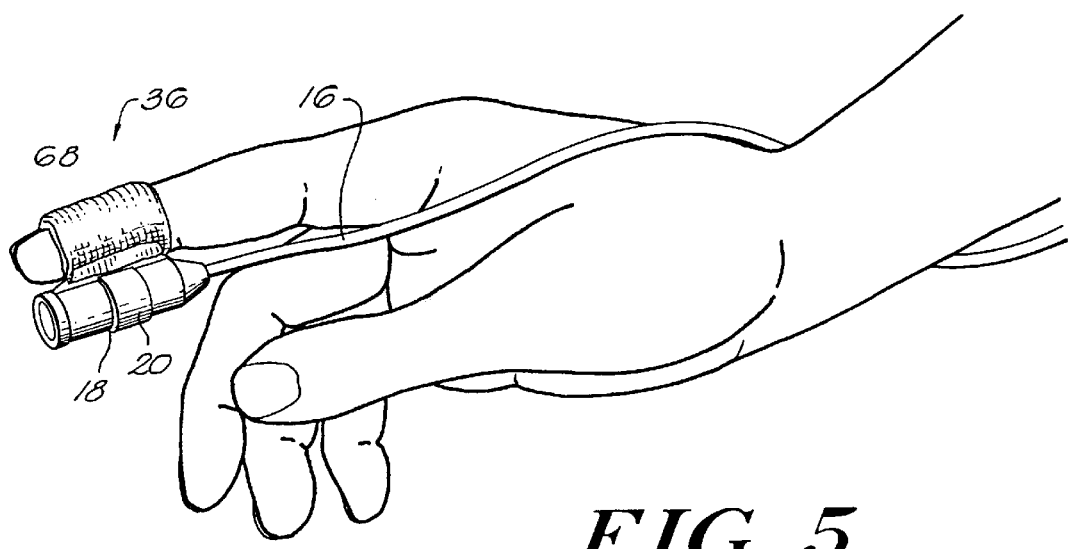
FIG. 5 shows a soft mount finger strap version of an endoscope system according to the invention.

An alternative version of the deployment assembly, namely a soft mount finger strap, is shown in FIG. 5. The soft mount finger strap 68 removably wraps around a surgeon's finger, preferably the surgeon's index finger. The finger strap carries a C-shaped connecting member 20 that removably and replaceably mounts with the imaging assembly housing 18.

Figure 6:
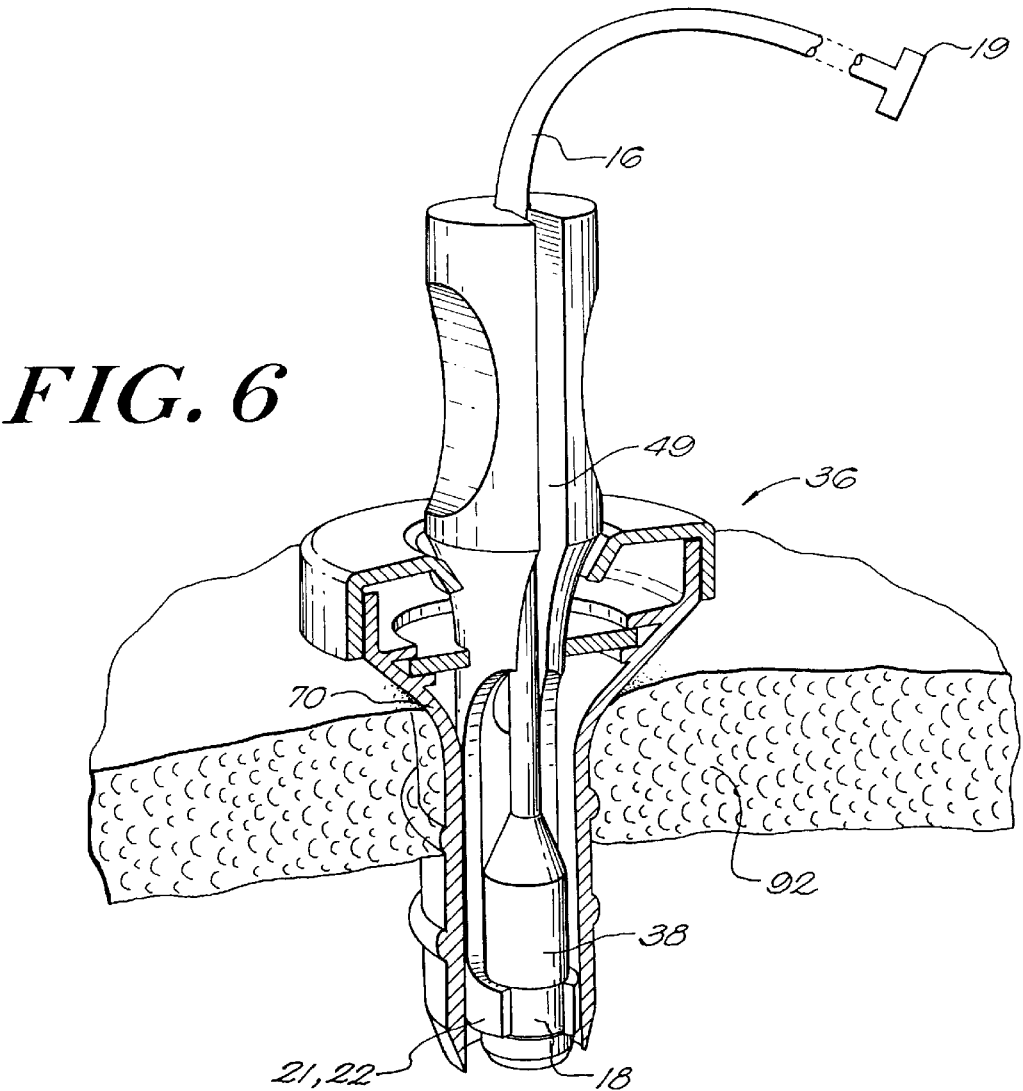
FIG. 6 shows a cannula mount version of an endoscope system according to the invention.

Yet another embodiment of the deployment apparatus, namely a cannula mount, is shown in FIG. 6. The cannula mount 70 is inserted into tissue; for example, a surgeon can insert a cannula mount into a patient's chest wall for viewing of the chest cavity during a thoracoscopic procedure. Again, the cannula mount carries a connecting member 20 that removably and replaceably mounts with the imaging assembly housing 18. Further, one version of the cannula mount incorporates a cable insertion channel 49 and retaining ribs 74 as illustrated in FIGS. 8B–8E.

It will thus be seen that the invention efficiently attains the objects set forth above, among those made apparent from the preceding description. Since certain changes can be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of scope of the invention which, as a matter of language, might be said to fall therebetween.

Having described the invention, what is claimed as new and desired to be secured by Letters Patent is:

1. An endoscope system comprising
 a) an imaging assembly having a distal end for detecting image information and a proximal end for delivering the image information to a remote location, said imaging assembly including
  an image detecting means located at the distal end of the imaging assembly for detecting image information,
  an image delivering means located at the proximal end of the imaging assembly for delivering the image information to a location remote from the image detecting means,
  an elongated, flexible cable assembly extending therebetween, and
  a housing surrounding at least a selected portion of the distal end of the imaging assembly, and
 b) deployment means for deploying said imaging assembly, said deployment means including
  a support member for supporting the imaging assembly, said support member including
   a shaft member having first and second ends,
   handle means connected to the first end of the shaft member for manual engagement of the deployment means,
   an articulating portion coupled to the second end of the shaft member and movable between undeflected and deflected positions for deflecting the tip of the imaging assembly, said articulating portion having a distal end, said articulating portion including a plurality of hingedly connected vertebrae collectively forming a spine for deflection of the articulating portion, and
   deflecting means attached in selected proximity to the distal end of the articulating portion for deflecting the articulating portion,
  said support member forming a cable insertion channel for insertion and removal of the imaging assembly cable, and
  a connecting member carried on the support member and removably and replaceably mountable with the imaging assembly housing for connecting the support member to the imaging assembly,
 so that a single imaging assembly is removably and replaceably mountable with any of plural deployment means.

2. The endoscope system of claim 1, wherein said deployment means further comprises
 imaging assembly guide means slidably and removably and replaceably mountable with the imaging assembly,
 such that an operator can manually, slidably extend the imaging assembly from the deployment means so as to position the imaging assembly's distal end in selected proximity to a target site.

3. The endoscope system of claim 1, wherein said cable assembly comprises
 a posable portion located in selected proximity to the imaging assembly's distal end for manually posing said imaging assembly distal end in selected proximity to a target site.

4. The endoscope system of claim 1, wherein the deflecting means comprises
 a deflecting cable affixed in selected proximity to the distal end of the articulating portion so that a proximal displacement of the deflecting cable relative to the articulating portion flexes the articulating portion.

5. The endoscope system of claim 1, wherein said support member comprises a soft-mount finger strap.

6. The endoscope system of claim 1, wherein said support member comprises a cannula.

7. The endoscope system of claim 1, wherein the endoscope system further comprises a lens protector assembly attached to the distal end of the imaging assembly.

8. The endoscope system of claim 1, wherein the handle means is coupled to the deflecting means for controlling the deflection of the articulating portion, and
 wherein the handle mechanism comprises a locking deflection control means coupled to the deflecting means for maintaining the deflection of the articulating portion.

9. The endoscope system of claim 4, wherein said deflecting cable is selected from the group of cables including a rigid wire and a flexible, braided cable.

10. The endoscope system of claim 7, wherein the lens protector assembly comprises
   a lens protector, and
   blade means extending outwardly from the lens protector for facilitating penetration of the distal end of the imaging assembly into tissue.

11. An endoscope system comprising
   a) an imaging assembly having a distal end for detecting image information and a proximal end for delivering the image information to a remote location, said imaging assembly including
      an image detecting means located at the distal end of the imaging assembly for detecting image information,
      an image delivering means located at the proximal end of the imaging assembly for delivering the image information to a location remote from the image detecting means,
      an elongated, flexible cable assembly extending therebetween, and
      a housing surrounding at least a selected portion of the distal end of the imaging assembly,
   b) deployment means for deploying said imaging assembly, said deployment means including
      a support member for supporting the imaging assembly, said support member including
         a shaft member having first and second ends,
         handle means connected to the first end of the shaft member for manual engagement of the deployment means,
         an articulating portion coupled to the second end of the shaft member and movable between undeflected and deflected positions for deflecting the tip of the imaging assembly, said articulating portion having a distal end, and
         deflecting means attached in selected proximity to the distal end of the articulating portion for deflecting the articulating portion, and
      a connecting member carried on the support member and removably and replaceably mountable with the imaging assembly housing for connecting the support member to the imaging assembly, so that a single imaging assembly is removably and replaceably mountable with any of plural deployment means, and
   c) a lens protector assembly attached to the distal end of the imaging assembly, the lens protector assembly comprises
      a lens protector,
      attachment posts connected to the lens protector, and
      first and second pin means for pivotally connecting the attachment posts to the sides of the distal end of the imaging assembly so that the lens protector assembly can pivot from a first removed position to a second covered position, the center point of the first pin means being located distally from the center point of the second pin means such that if an operator pivots the lens protector from the first position toward the second position a spring energy is created by the mismatch of the center points of the first and second pin means, causing the lens protector assembly to snap either to the first position or to the second position.

12. An endoscope system comprising
   a) an imaging assembly having a distal end for detecting image information and a proximal end for delivering the image information to a remote location, said imaging assembly including
      an image detecting means located at the distal end of the imaging assembly for detecting image information,
      an image delivering means located at the proximal end of the imaging assembly for delivering the image information to a location remote from the image detecting means,
      an elongated, flexible cable assembly extending therebetween, and
      a housing surrounding at least a selected portion of the distal end of the imaging assembly,
   b) deployment means for deploying said imaging assembly, said deployment means including
      a support member for supporting the imaging assembly, and
      a connecting member carried on the support member and removably and replaceably mountable with the imaging assembly housing for connecting the support member to the imaging assembly, so that a single imaging assembly is removably and replaceably mountable with any of plural deployment means, and
   c) a lens protector pivotally connected to the distal end of the imaging assembly for protecting the image detecting means during insertion of the distal end of the imaging assembly,
   such that said lens protector can be manually removed from the central field of view of the image detecting means subsequent to insertion of the distal end of the imaging assembly.

13. A deployment device for deploying an imaging assembly, wherein
   said imaging assembly has a distal end that detects information and a proximal end that delivers the image information to a remote location, said imaging assembly including
      an image detecting element located at the distal end of the imaging assembly for detecting image information,
      an image delivering element remote from said image detecting means for delivering the image information,
      an elongated, flexible cable assembly extending therebetween, and
      a housing surrounding at least a selected portion of the distal end of the imaging assembly,
   said deployment device comprising
      a support member for supporting the imaging assembly, said support member including
         a shaft member having first and second ends,
         handle means connected to the first end of the shaft member for manual engagement of the deployment device,
         an articulating portion coupled to the second end of the shaft member and having a multi-part structure movable between undeflected and deflected positions, said articulating portion having a distal end, said articulating portion including a plurality of hingedly connected vertebrae collectively forming a spine for deflection of the articulating portion, and deflecting means attached in selected proximity to the distal end of the articulating portion for deflecting the articulating portion, said support member forming a cable insertion channel for insertion and removal of the imaging assembly cable, and a connecting member carried on the support member and removably and replaceably mountable with the imaging assembly housing.

14. The deployment device of claim 13, wherein the deflecting means comprises a deflecting cable affixed in selected proximity to the distal end of the articulating portion so that a proximal displacement of the deflecting cable relative to the articulating portion flexes the articulating portion.

15. The deployment device of claim 13, wherein the handle means is coupled to the deflecting means for controlling the deflection of the articulating portion, and wherein the handle mechanism comprises a locking deflection control means coupled to the deflecting means for maintaining the deflection of the articulating portion.

\* \* \* \* \*